United States Patent [19]

Thurn et al.

[11] Patent Number: 4,859,062
[45] Date of Patent: Aug. 22, 1989

[54] OPTOELECTRICAL MEASURING SYSTEM AND APPARATUS

[76] Inventors: Gerhard Thurn, Otto-Suhr-Allee 143, 1000 Berlin 10; Theodor Gast, Bergstr. 1, D-1000 Berlin 39, both of Fed. Rep. of Germany

[21] Appl. No.: 693234

[22] Filed: Jan. 22, 1985

Related U.S. Application Data

[63] Continuation of Ser. No. 301,969, Sep. 14, 1981.

[30] Foreign Application Priority Data

Oct. 4, 1980 [DE] Fed. Rep. of Germany ....... 3037622

[51] Int. Cl.$^4$ .................. G01B 11/30; G01N 21/55
[52] U.S. Cl. .................... 356/371; 356/446
[58] Field of Search ................. 356/371, 446

[56] References Cited

U.S. PATENT DOCUMENTS

| | | | |
|---|---|---|---|
| 3,060,793 | 10/1962 | Wells | 356/369 |
| 3,782,827 | 1/1974 | Nisenson et al. | 356/447 |
| 3,904,293 | 9/1975 | Gee | 356/369 |
| 3,922,093 | 11/1975 | Dandliker et al. | 356/448 |
| 4,076,421 | 2/1978 | Kishner | 356/446 |
| 4,162,126 | 7/1979 | Nakagawa et al. | 356/446 |
| 4,285,597 | 8/1981 | Lamprecht et al. | 356/446 |
| 4,334,780 | 6/1982 | Pernick | 356/446 |
| 4,368,982 | 1/1983 | VanArnan et al. | 356/445 |

FOREIGN PATENT DOCUMENTS 145956 1/1981 German Democratic Rep. ................. 356/446

OTHER PUBLICATIONS

Spiegel, *Statistics*, Schaum's Outline Series, McGraw-Hill, N.Y., 1961, Chapter 4, pp. 69 through 73.

Moan, O. B., "Application of Mathematics and Statistics to Reliability and Life Studies", in *Reliability Handbook*, Irsson, Editor-in-Chief, McGraw-Hill, N.Y., 1966, pp. 4-8 through 4-50.

Primary Examiner—Richard A. Rosenberger
Attorney, Agent, or Firm—Bauer & Schaffer

[57] ABSTRACT

The invention relates to measuring the surface roughness of a sample. A beam of light is directed onto the surface and the scattered light distribution is measured using a detector array. Either the average deviation or the second moment of the scattered light distribution is then determined, which are measures of the surface roughness.

21 Claims, 4 Drawing Sheets

OPTOELECTRICAL MEASURING SYSTEM AND APPARATUS

This is a continuation of U.S. Ser. No.: 301,969 Filed: 9/14/81

This invention relates to an optoelectronic measuring method for determining the surface quality of dispersively reflecting surfaces, in particular on metallic work pieces, in which the surface to be examined is illuminated by a generally parallel beam of rays from a light source and the intensity distribution of the reflected radiation is measured and evaluated electronically by photoelectric detectors, and to apparatus for implementing the measuring method.

Measuring methods and apparatus of this type are extremely significant for ensuring the quality of mechanically manufactured work pieces, because the observance of a specific surface quality, for example, on fitting surfaces, close surfaces, friction surfaces and lacquered surfaces is essential for the function of the respective component part.

Various methods and devices are known for measuring the surface quality or surface roughness. Stylus instruments are used very frequently for measuring roughness. They have a small probe in which a diamond needle mechanically traces the surface. The measured values are recorded and/or registered in an amplified manner. These devices have attained a high technical level. A disadvantage is the linear tracing of the surface and the time-consuming measuring procedure which cannot be carried out free of contact and may only be automated with difficulty.

In the book 'Technische Oberflächenkunde', Verlag J. Springer, Berlin 1936, G. Schmaltz describes a measuring method on pages 98 to 99, in which the backscatter indicatrix which is detected using movable photodetectors is evaluated photometrically. Either a factor is used as a measurement for the surface quality, which factor describes the approximation of the scattered light curve to a Gaussian distribution, or the half-power angle is used, at which the radiation intensity is reduced to half the intensity which is radiated at the specular reflection angle. This method starts out in a restrictive manner from a Gaussian distribution of the scattered light curve, or only two measured values for characterising the surface quality are used from the complete scatter curve. Apart from the fact that the pre-requisite of a Gaussian distribution of the scattered light curve is not provided for most surface structures, the evaluation which is based on only two measuring points leads to inaccurate measuring results.

A measuring apparatus is known from German Auslegeschrift No. 2,260,090 which uses the half-power width of the scattered light distribution about the specular reflection angle of between 60° and 85° angle of incidence as a measurement for the roughness. This measurement is formed from a total of three measuring points of the scattered light distribution, that is, the measured value at the peak of the curve and the respective half-values. In this case, there is a disadvantage in that the half-width value is not clearly defined on flat or multiple-peak distribution curves, as occurs in technical roughnesses and it is an unreliable measurement in the statistical sense. Chance fluctuations in the measured values, in particular in the maximum value which represents the reference value have a direct effect on the measuring result. The flat incidence of light necessary for measuring renders the measuring arrangement sensitive to changes in spacing and due to its large dimensions, the measuring apparatus may only be used when there is enough space and time available for the complicated handling.

Furthermore, a method is known from the publication by F. Piwonka und Th. Gast in "Technisches Messen" (1979) 12, P. 451–458 in which rotating photoreceivers are used to record the backscatter indicatrix and the depth of roughness is calculated therefrom. This method may only be applied to surfaces which are machined periodically, for example on a rotary machine, because the groove width of the rough grooved surface must be known. The measuring range of this arrangement only covers the coarse range of surface roughness.

Another method for measuring roughness is known from German Patent No. 2,241,617 which operates with a laser. In this method, the flat measuring sample is rotated mechanically and the angular-dependent light reflected back in the direction of incidence is measured. The probability distribution of the partial derivatives of the roughness profile is calculated from the light distribution. The physical boundary conditions to be observed in this method and the necessary relative movement of the measuring apparatus and of the object to be measured considerably restrict the area of use.

Furthermore, methods for measuring roughness are known from the literature which evaluate the "speckle" pattern in the scatter field of the reflected light. For this purpose, an illumination apparatus is necessary which meets certain coherency conditions, for example, a laser.

An object of the present invention is to provide a measuring method and measuring apparatus which allow a surface quality to be determined more accurately using simple and manageable devices.

Using the measuring apparatus, measurements on flat, convex and concave measuring surfaces and at difficult measuring points such as on bevels, in grooves and bores may be carried out free of contact or with gentle contact in a rapid measuring sequence. The measuring apparatus may be operated manually and it may also be easily incorporated into automatic apparatus, in which case it is unnecessary to work with coherent light.

Based on the initially-mentioned measuring method, this object is achieved according to the present invention in that a beam of rays is directed generally perpendicularly onto a surface to be examined and the spatially distributed reflected radiation coming out from the illuminated surface section (measuring spot) is detected by photoelectric detectors at a solid angle which is adapted to the spread to be expected of the beam as a result of the scatter reflection and that integral characteristic values are formed from all of the measured values established by the detectors as a measurement for the surface quality. Further developments of the measuring method according to the present invention and of the apparatus for implementing the method are specified in the subclaims.

The basic concept of the present invention essentially lies in detecting the scattered radiation reflected by the measuring spot using a measuring tube at a solid angle which is adapted to the scatter and thus to the expected quality range of the surface to be examined and in forming integral characteristic values $S_x$ from the intensity values measured with detectors in the manner of power moments known from mechanics and statistics, which characteristic values $S_x$ are used as a measurement for the surface quality.

The following equations are used to form the characteristic values:

$$S_x = \sum_{i=1}^{n} |w_i - \bar{w}|^x \cdot p_i \text{ where } x = 1 \text{ or } 2 \quad \text{(a)}$$

$$w = \sum_{i=1}^{n} w_i \cdot p_i \quad \text{(b)}$$

$$p_i = \frac{D_i \cdot g_i}{\sum^n D_i \cdot g_i} \quad \text{(c)}$$

The reference in the equations represent the following:
$w_i$ the angle of the scattered radiation detected by the respective detector i
n the number of detectors used for evaluation
$\bar{w}$ the average from values $p_i$ and $w_i$
$p_i$ measurement signal $D_i$ standardized according to the equation (c)
$g_i$ correction factor for the measurement signal $D_i$.

In the method according to the present invention, values $p_i$ standardized according to the equation (c) are obtained from the measured signals of the detectors n which are preferably positioned in a row, taking into account the correction factors $g_i$. In contrast to the known methods and arrangements described above, the measurement signals of all the detectors recording the reflected radiation enter into the evaluation. Due to the formation of the quotient $p_i$, only the scatter characteristics of the surface structure are evaluated and the material-conditioned spectral reflection coefficients remain without influence on the measuring result. An average $\bar{w}$ is calculated from the values $p_i$ and the values $w_i$. The characteristic values $S_1$ or $S_2$ are formed last of all. The quadratic scatter characteristic value $S_2$ is the statistically reliable value. On the other hand, it is easier to calculate the characteristic value $S_1$.

The correction factors $g_i$ are to balance manufacturing tolerances in the electrical and optical characteristic values of the construction elements used and to correct the changes in the scattered light distribution determined in a geometrically-optical manner by optical construction elements.

For this purpose, the factors lying between 0 and 1 are determined in a measuring procedure with a comparative surface of known scatter.

Moreover, it is also possible by approximation of these factors to influence the characteristic line path of $S_1$ or $S_2$ over a greater range of the surface quality by a different weighting of the scattered light curve, for example in order to carry out a linearisation, and to emphasize or suppress specific parts of the scattered light curve, for example, in order to evaluate separately scattered light or regularly reflected light.

The advantages of the present invention are mainly found in the following facts:
the surface quality is determined as an average over a measuring spot;
integral characteristic values $S_1$ or $S_2$ are formed which allow a reliable and accurate statement even in the case of randomly formed scattered light curves, and the type of distribution, for example Gaussian distribution, does not have to be known;
the characteristic value formation includes all detectors, and chance fluctuations in the scattered light curve, as caused by alignment errors or statistical irregularities of the surface, are averaged out;
the integral characteristic values are invariant to a swing in the scattered light distribution in the measuring plane;
optical quality features of the surface, such as, for example, the scatter behaviour and structural features are exactly described by the characteristic values $S_1$ or $S_2$;
there is a close, very effectively reproducible connection between the characteristic values $S_1$ or $S_2$ and standardized roughness characteristic quantities when the fabrication conditions are known;
by adapting the solid angle detected by the measuring apparatus to the angle of the scattered radiation, a large measuring range is achieved which extends from $R_a > 0.01$ μm to $R_a < 10$ μm, oriented at the average roughness value $R_a$;
separate determination of transverse and longitudinal roughness is possible by rotating the measuring plane;
the measuring arrangement is insensitive to changes in spacing due to the generally perpendicular irradiation;
the measurement may be carried out with gentle contact or free of contact manually or automatically even at difficulty accessible measuring points; and
measurements on stationary and on moving surfaces are possible.

The characteristic values $S_1$ or $S_2$ may be determined in an electronically analog or digital manner. It is preferred to calculate the characteristic value in a computer because this easily allows measured data to be stored, and allows an interactive operation control and a comprehensive documentation of the measuring results.

In order to adjust a specific characteristic line path of the characteristic values $S_1$ or $S_2$ over a range of the surface qulity, the characteristic values are to be multiplied in the computer with a scale factor and/or powers of the characteristic values are to be used. Standardized roughness characteristic quantities such as the average roughness $R_a$ or the averaged roughness depth $R_z$ are determined indirectly via measuring procedures. Surfaces of known roughness are measured optically and the characteristic quantities $S_1$ or $S_2$ are related to stylus characteristic quantities. The relevant characteristic line is stored in a computer. In order to achieve a high measuring accuracy, it is appropriate to measure and store several characteristic lines corresponding to the conventional processing methods.

Another possibility is to vary the wave length range of the measured radiation in order to adjust different scatter angle ranges. The scattering on surfaces of a specific roughness is greater with short wave lengths, for example UV light, compared to long wave lengths, for example IR light. The radiation used does not have to be monochromatic, but it may extend over a greater wave length range, for example, 100 nm.

Another possibility is to use polarized measured radiation. During the reflection of polarized radiation, rough surfaces exhibit a behaviour which differs from smooth surfaces and from which the surface quality may be deduced by considering the orientation of the polarisation plane of the radiation to the structure of the surface. Thus, the characteristic values $S_1$ or $S_2$ may be used as a measurement for the surface quality from the polarisation condition of the radiation within the reflected radiation beam.

The invention is described in the following with reference to embodiments of the measuring apparatus. The drawings illustrate schematic views.

Figure 1:
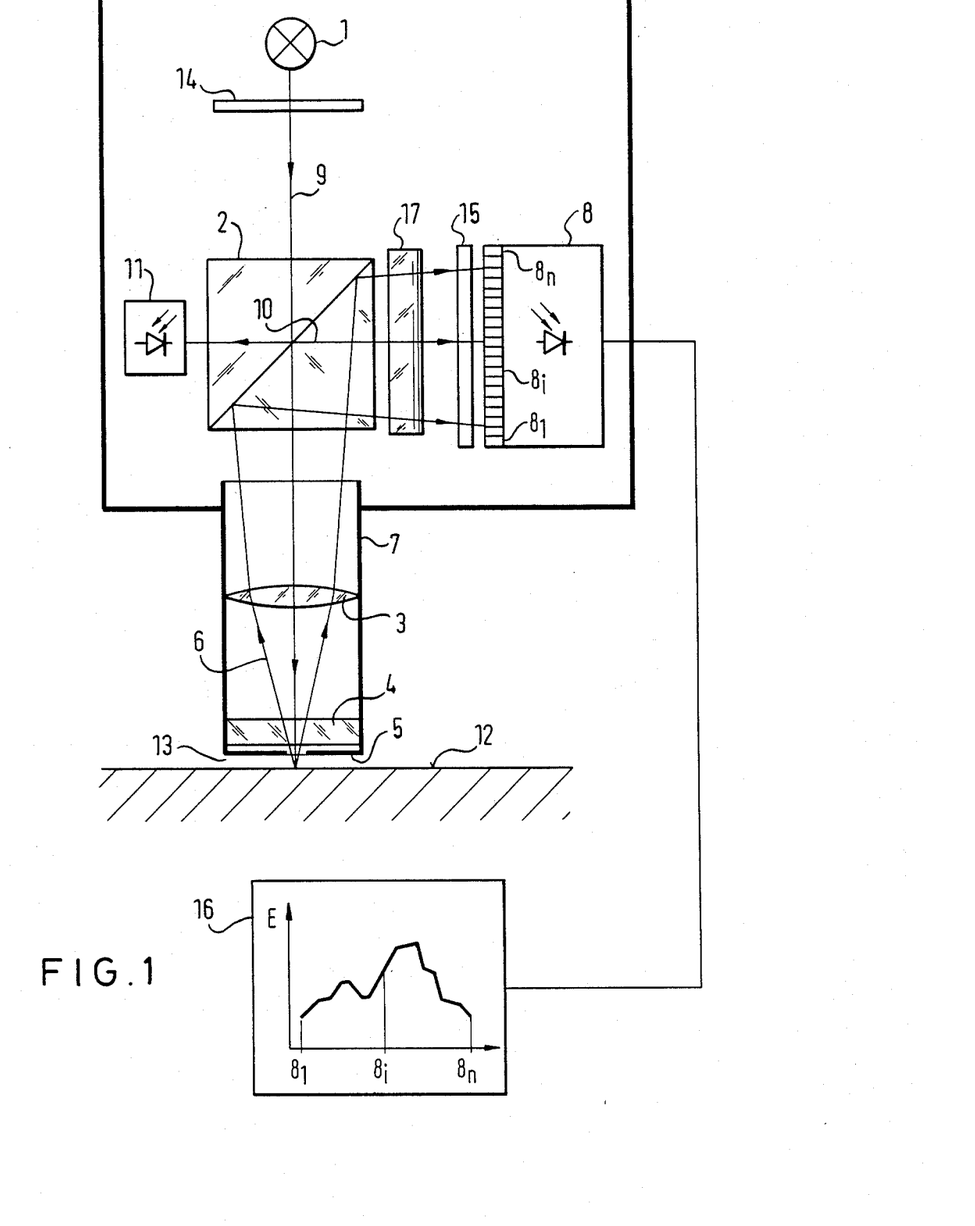
FIG. 1 illustrates a scattered light measuring apparatus according to the present invention.

In the measuring apparatus according to FIG. 1, a beam source 1 is provided, for example, a diode emitting infrared light having a glass lens which is attached thereon and whose concentrated, generally parallel radiation 9 passes through a beam splitter 2, a lens system 3 and a plane-parallel glass plate 4. The measuring spot is restricted by a circular diaphragm 5 to about from 1 to 3 mm in diameter. The system is completely encapsulated by the glass plate 4. The direction of the radiation 6 reflected by the surface 12 is changed by the refractive power of a lens system 3 and the radiation 6 passes back through the beam splitter which outwardly reflects as large a partial flux as possible to the photoelectric detectors 8. Photodiodes or pyroelectric detectors may be used individually or in the embodiments as a linear array or a matrix array, as the detectors $8_1$, $8_i$ to $8_n$. The detectors convert the radiation into electrical signals which are further processed in analog or digital manner, having been filtered and amplified, such that they state the scatter characteristic values $S_1$ or $S_2$ as a measurement for the surface quality. The path of the intensity of irradiation E is indicated on a screen 16, this path being measured by the detectors $8_1$ to $8_n$. In order to improve the disturbance signal-to-noise ratio, the detectors are provided with an optical filter which narrows the spectral range of reception to the wave length range of the beam source.

A further improvement arises from working in variable light operation. For this purpose, the light of the beam source is pulsed electrically or optically with a specific frequency and the measurement signal is evaluated in a frequency-selective manner. The measuring tube 7 determines the solid angle with its dimensions, in particular its length and with the lens system 3 contained therein and with the glass plate 4, the reflected radiation being supplied to the detectors $8_1$ to $8_n$ at this solid angle. In the simplest case, the lens system 3 may be omitted. The solid angle then results from the geometrical data of the measuring apparatus, substantially from the aperture angle of the detector row 8. Lens systems having a positive focal distance enlarge the solid angle; dispersing lenses narrow this angle.

In the method according to the present invention, it is unnecessary to position the detectors in the focal plane of the lens system or to carry out a real representation of the illuminated surface section, as a result of which, advantages are provided in the dimensioning of the measuring tube.

Several measuring tubes which may be mutually exchanged and which differ in their optical characteristic data are provided for each measuring apparatus. This allows an adaption to the scatter angle range which is to be expected during a measurement and which results from the range of the surface quality of the surface to be examined. The range of the surface quality is provided by the surface processing method which takes place before measuring, for example, fine rotation, surface grinding or polishing. The respective appropriate measuring tube is selected based thereon.

According to FIG. 1, a cylinder lens 17 is inserted into the beam path of the scattered light. This lens collects the spatially distributed scattered radiation into a band of light in the measuring plane which is defined by the centre beams 9 and 10 and in which is located the row 8 of detectors. As a result of this measure, the disturbing influence of the beam scatter on convex surfaces is reduced and the useful radiation flux is increased. This cylinder lens may be integrated into the lens system 3. It is even advantageous to construct the lens system 3 from a system of crossed cylinder lenses, the focal distance of which is selected such that the scattered radiation is detected in one plane at the angle which is most favourable for determining the surface quality and in the other plane, the reflected radiation is collected into a band of light in which the detectors 8 are located. In the case of lenses having a high refractive power, it is appropriate to flatten them in the centre, so that the incident beam remains unchanged, while the dispersively reflected radiation is refracted by the curved lens surfaces. This optical intervention is compensated during electronic processing of the measured values.

Another photoelectric detector 11 (reference detector) measures the part, branched off by the beam splitter 2, of the beam 9 coming from the beam source 1. The beam intensity fluctuations thereof are compensated in the measured data processing operation via a quotient and/or subtraction circuit. The measurement may take place with slight contact in that the small manageable scattered light measuring apparatus is positioned with the measuring tube 7 generally perpendicularly on the surface 12 to be measured. Since the supporting surface of the measuring tube is relatively large and only small forces are prevalent, the surface to be measured is substantially prevented from being damaged. For measuring very sensitive surfaces, the supporting surface of the measuring tube should be made of a non-rigid material, for example, a plastics material. Contact-less measurement is achieved by adjusting a small measuring spacing 13 and thus, a measurement is also possible on moving surfaces. This type of operation may also be advantageously applied in automatic apparatus.

In order to determine the surface characteristic quantities, termed transverse or longitudinal roughness in roughness measuring technology on directional rough structures, for example, on grooved roughness, the measuring device may be oriented with its measuring plane transversely or longitudinally to the direction of the grooves. Another possibility of measuring the direction-dependent scatter characteristics of a surface without rotating the measuring device about 90° during this measurement lies in a matrix arrangement consisting of several rows of detectors or in an arrangement of crossed rows of detectors. In the latter case, a second row of detectors is positioned perpendicularly to the row 8 of detectors and this second row detects the reflected radiation perpendicularly to the measuring plane. A possibility of expanding the measuring range of the apparatus provided by the geometry and the optical system of the measuring tubes consists in changing the wave length of the radiation used. For this purpose, either the light of the beam source 1 is monochromatic, or a filter is used to screen a specific wave length range from a beam source which has a broad spectrum.

Another possibility is to measure scattered light using polarized radiation. For this purpose, a polarisation filter 14 is provided in the arrangement to produce polarized radiation and a polarisation filter 15 is also provided to analyse the reflected radiation.

Figure 2:
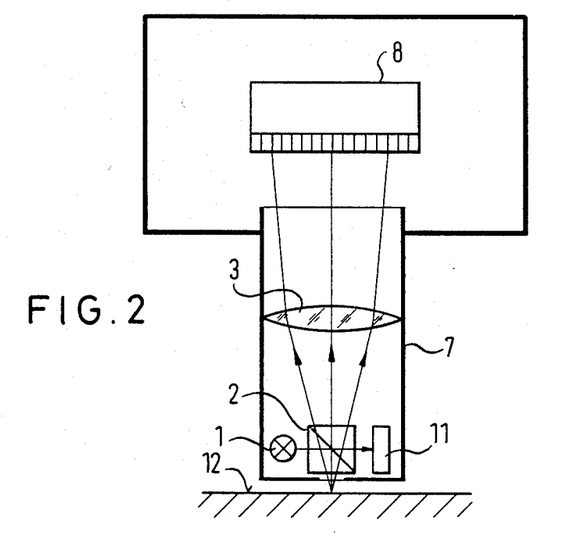
FIG. 2 illustrates a view of a measuring apparatus with a beam source in a measuring tube.

According to FIG. 2, the measuring apparatus according to FIG. 1 is modified such that the beam source 1, for example a small semiconductor beam source, is located in the measuring tube 7. The advantage of this arrangement is the fact that the beam of rays from the beam source 1 does not enter via the lens system 3, but the scattered radiation is detected by the lens system. As a result of this, the scattered radiation may be detected in a large solid angle which is necessary for the coarse roughness range. In this arrangement, the beam splitter 2 is positioned between the beam source 1 and the reference diode 11, while the row 8 of detectors is located in the housing of the apparatus.

Where there are unfavourable spatial conditions, it is advantageous to use a light guide, for example, in order to measure inside surfaces of work pieces or inside the processing machine using the apparatus. An ordered optical-fibre bundle may be used as a light guide, the cross section of which may be rectangular or circular and/or fibre optical cross-section transducers may be used. In the arrangement according to FIG. 1, the light guide is preferably inserted between the measuring tube 7 and the beam splitter 2 and it guides both the incident radiation as well as the reflected radiation. A light guide may also be used in the arrangement according to FIG. 2 for guiding the reflected radiation. It is appropriately positioned between the measuring tube 7 and the row 8 of detectors.

Figure 3:
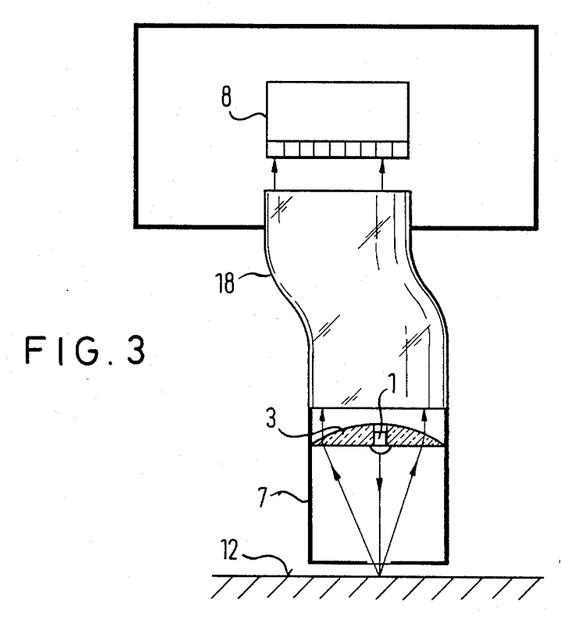
FIG. 3 illustrates a measuring apparatus with a flexible light guide.

FIG. 3 illustrates an arrangement in which the beam source 1 is again located in the measuring tube 7 and is inserted directly into the lens system 3. Since the beam splitter has been omitted, the useful radiation of the beam source is increased. In this case, the reflected light flux is supplied to the detectors 8 via a flexible light guide 18. In order to illuminate the surface section to be measured, another light guide having a small diameter may be used which is positioned concentrically to the light guide 18. This additional light guide is to be provided separately from the light guide 18 in the housing of the apparatus and it allows the light of a high power beam source to be supplied to the measuring point.

Figure 4:
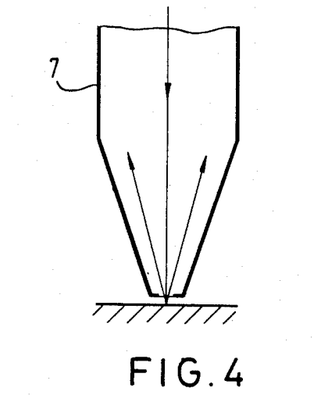
FIG. 4 illustrates a measuring tube having a conical point.

FIG. 4 illustrates an embodiment of a measuring tube having a conical measuring point. This shape of the measuring tube is suitable for spatially confined measuring points.

Figure 5:
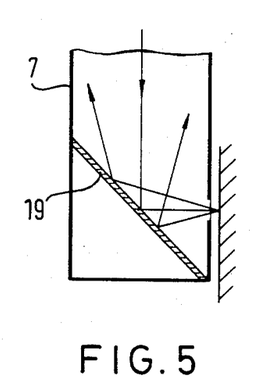
FIG. 5 illustrates a measuring tube having a lateral beam outlet.

FIG. 5 schematically illustrates another embodiment of the measuring tube, in which the light escapes at the side through a deflecting mirror 19, which is advantageous, for example, for measurements in a bore or in a groove of a work piece.

Figure 6:
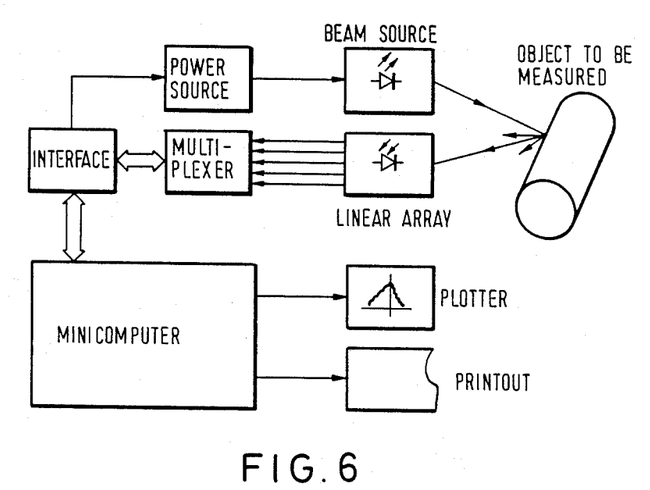
FIG. 6 illustrates a block diagram of the measuring system with a computer for processing the measured values, and FIG. 7 graphically illustrates the dependence of the characteristic value $S_2$ on the surface quality of different samples of surfaces.

FIG. 6 illustrates a block diagram of the measuring system. A computer is used to process the measured values. Several scattered light sensors may be connected to this basic electronic device. The measuring procedure is clarified in the block diagram. A light-emitting diode is fed by a power source and it illuminates the surface to be measured of the measuring object. The photodiodes of a linear array convert the reflected light flow into electrical signals which are supplied to the electronics (shown with interface) via multiplexers and controlled by the computer. The signals are filtered in the electronics, amplified and are available to the computer for further processing as digital values after an analog-digital conversion. The result of the measurements is recorded or presented graphically on a screen or on a plotter.

Figure 7:
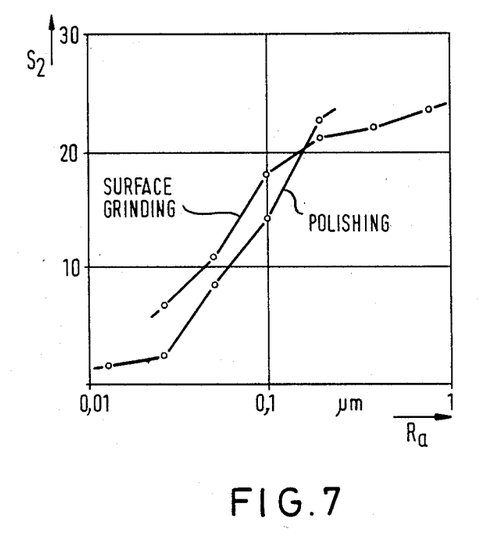

Characteristic curves are shown in FIG. 7 which have been produced from comparative measurements of the method according to the present invention with stylus measurements on surface-ground and polished surface samples. The scatter characteristic value $S_2$ is dimensionless and is plotted, multiplied with a scale factor against the average roughness value $R_a$ which was measured using a stylus device.

The apparatus which has been described is provided for determining the surface quality of flat, concave or convex metallic surfaces. In addition thereto, it is possible using this measuring apparatus to also determine the surface quality of parts made of other materials, for example, semiconductor materials, plastics and porcelain.

A measuring method similar to the one according to the present invention may also be used for determining the surface quality or the scatter behaviour of work pieces made of transparent material, for example, glass. In this method, the work piece to be examined is illuminated from the work piece surface opposite the measuring head and the penetrating light is spread and scattered by the irregular structures. The scattered light distribution is then generally measured in the same manner as described above for the reflected scattered light.

We claim:

1. Apparatus for determining the roughness and structure, respectively, of a surface area of workpieces, said apparatus comprising a source of light having a beam, the rays of which are substantially parallel and directed substantially perpendicularly onto the surface area to be examined; a plurality of detectors arranged in an array so that each said detector senses the light scattered from said surface area within a given solid angle to measure the light intensity at a scattering angle in the distribution different from that measured by the other detectors, and an analyzing circuit means responsive to the outputs of said detectors to determine an integral characteristic value from the values of intensity measured by said detectors and from the scattering angles to thereby analyze and determine the surface roughness and structure, respectively, in the following manner:

(a) at first determining standardized light intensity values $p_i$ according to the equation $$p_i = \frac{D_i \cdot g_i}{\sum_{i=1}^{n} D_i \cdot g_i}$$

wherein $D_i$ is the light intensity of the scattered light measured by the respective detector i, n is the number of detectors, and $g_i$ is a correction factor for the respective light intensity value $D_i$;

(b) then determining an average angle $\bar{w}$ of the scattered light by the detectors i from the values $p_i$ and the scattering angles according to the equation:

$$\bar{w} = \sum_{i=1}^{n} w_i \cdot p_i$$

wherein $w_i$ is the scattering angle at which the respective detector i measures the intensity of the scattered light; and (c) at last determining an integral characteristic value $S_x$ from from the value $\bar{w}$ and the values $p_i$ and $w_i$ according to the equation:

$$S_x = \sum_{i=1}^{n} |w_i - \bar{w}|^x \cdot p_i$$

where $x = 1$ or $2$.

2. The apparatus according to claim 1 including means for varying the wave length of the measured radiation to change the scatter angle of the reflected radiation.

3. The apparatus according to claim 1, including means for polarizing the incident beam on the surface area to be examined.

4. The apparatus according to claim 3, including an analyzer in the path of said incident beam and a polarizer arranged in the path of said reflected beam.

5. The apparatus according to claim 1, including means for rotating the measuring plane to establish a directional-dependence of the reflection behaviour of surfaces having a directed (anisotropic) rough structure.

6. The apparatus according to claim 1, including means for supplying at least some of the incident radiation to a reference photodetector and compensating for fluctuations in the beam intensity by the output signal of the photodetector via an analog or digital circuit.

7. The apparatus according to claim 1, comprising a measuring tube positioned approximate to the surface to be examined, said tube having a diaphragm and the solid angle of the scattered radiation which may be detected by the detectors is determined by the length and/or optical characteristics of the tube.

8. The apparatus according to claim 7, including a lens system within said measuring tube.

9. The apparatus according to claim 8, wherein said lens system includes a cylinder lens for collecting the scattered radiation into a band of light, and said photoelectric detectors are positioned in a row, as a linear photo array are located.

10. The apparatus according to claim 9, wherein the lens system is formed from crossed cylinder lenses, one of which detects the scattered radiation at the respective solid angle and the other collects the scattered radiation into a band of light in which the row of detectors is positioned.

11. The apparatus according to claim 8 wherein the lenses of the lens system are flattened in their centre, so that the incident beam of rays is unchanged while passing through the system, but the dispersively reflected radiation is refracted by the lenses.

12. The apparatus according to claim 7, wherein the measuring tube is tightly sealed from said diaphragm by a plane-parallel glass plate.

13. The apparatus according to claim 7, including a beam splitter positioned in the path of the incident beam to the reference detector and for deflecting at least a part of the reflected radiation to the row of measuring detectors.

14. The apparatus according to claim 7 wherein the source of light is very small, and is positioned in the measuring tube between the lens system and the diaphragm.

15. The apparatus according to claim 14, wherein the light source is integrated into the lens system.

16. The apparatus according to claim 7, including a light guide provided between the measuring tube and the row of detectors for guiding the incident beam and/or the reflected radiation.

17. Apparatus according to claim 1 wherein the light directed from said source of light to said surface area is passed through the same lens as said light scattered from said surface area and directed onto said detectors.

18. Method for determining the roughness and structure, respectively, of a surface area of workpieces, particularly of metallic workpieces, wherein said method comprises:

(a) directing a beam of light, the rays of which are substantially parallel and substantially perpendicular onto the surface area to be examined;

(b) detecting the light scattered from said surface area at each one scattering angle of a plurality of scattering angles $w_i$ by means of an array of n detectors;

(c) measuring the individual detector signals $D_i$ of each of the detectors to obtain a plurality of detector signals;

(d) determining standardized detector signals $p_i$ by summing up said individual detector signals $D_i$ to obtain the sum of said individual detector signals and dividing each of said individual detector signals $D_i$ by said sum of said individual detector signals to obtain a plurality of quotients $p_i$ as standardized detector signals associated with each one of said detectors;

(e) determining an average angle $\bar{w}$ of the scattered light from the standardized detector signals $p_i$ and the scattering angles $w_i$; according to the formula $$\bar{w} = \sum_{i=1}^{n} w_i \cdot p_i$$

(f) determining a characteristic value $S_1$ of roughness and structure, respectively from the average angle $\bar{w}$ and the values $p_i$ and $w_i$ by subtracting said average angle $\bar{w}$ from each of said individual scattering angles $w_i$ to obtain a plurality of differences $w_i - \bar{w}$ of said scattering angles and said average angle $\bar{w}$, multiplying the absolute values $|w_i - \bar{w}|$ of each of said differences by the respective of said standardized detector signals $p_i$ to obtain products $|w_i - \bar{w}| \cdot p_i$, and summing up the plurality of said products $|w_i - \bar{w}| \cdot p_i$ to obtain said characteristic value $S_1$ of roughness and structure, respectively.

19. Method for determining the roughness and structure, respectively, of a surface area of workpieces, particularly of metallic workpieces, wherein said method comprises:

(a) directing a beam of light, the rays of which are substantially parallel and substantially perpendicular onto the surface area to be examined;

(b) detecting the light scattered from said surface area at each one scattering angle of a plurality of scattering angles $w_i$ by means of an array of n detectors;

(c) measuring the individual detector signals $D_i$ of each of the detectors to obtain a plurality of detector signals;

(d) determining standardized detector signals $p_i$ by summing up said individual detector signals $D_i$ to obtain the sum of said individual detector signals and dividing each of said individual detector signals $D_i$ by said sum of said individual detector signals to obtain a plurality of quotients $p_i$ as standardized detector signals associated with each one of said detectors;

(e) determining an average angle $\overline{w}$ of the scattered light from the standardized detector signals $p_i$ and the scattering angles $w_i$, according to the formula $$\overline{w} = \sum_{i=1}^{n} w_i \cdot p_i$$

(f) determining a characteristic value $S_2$ of roughness and structure, respectively from the average angle $\overline{w}$ and the values $p_i$ and $w_i$ by subtracting said average angle $\overline{w}$ from each of said individual scattering angles $w_i$ to obtain a plurality of differences $w_i - \overline{w}$ of said scattering angles $w_i$ and said average angle $\overline{w}$, determining the second powers of the absolute values $|w_i - \overline{w}|$ of each of said differences, multiplying second powers of the absolute values $|w_i - \overline{w}|$ of each of said differences by the respective of said standardized detector signals $p_i$ to obtain products $|w_i - \overline{w}|^2 . p_i$, and summing up the plurality of said products $|w_i - \overline{w}|^2 . p_i$ to obtain said characteristic value $S_2$ of roughness and structure, respectively.

20. Method for determining the roughness and structure, respectively, of a surface area of workpieces, particularly of metallic workpieces, wherein said method comprises:

(a) directing a beam of light, the rays of which are substantially parallel and substantially perpendicular onto the surface area to be examined;

(b) detecting the light scattered from said surface area at each one scattering angle of a plurality of scattering angles $w_i$ by means of an array of n detectors;

(c) measuring the individual detector signals $D_i$ of each of the detectors to obtain a plurality of detector signals;

(d) determining corrected standardized detector signals $p_i$ by multiplying each one of said detector signals $D_i$ by each one of individual correction factors $g_i$ associated to each one of said detectors, summing up the obtained products $D_i.g_i$ and dividing each of said products $D_{i.gi}$ by the sum of said products $D_{i.gi}$, to obtain said corrected standardized detector signals $P_i$;

(e) determining an average angle $\overline{w}$ of the scattered light from the corrected standardized detector signals $p_i$ and the scattering angles $w_i$, according to the formula $$\overline{w} = \sum_{i=1}^{n} w_i \cdot p_i$$

(f) determining a characteristic value $S_1$ of roughness and structure, respectively from the average angle $\overline{w}$ and the values $p_i$ and $w_i$ by subtracting said average angle $\overline{w}$ from each of said individual scattering angles $w_i$ to obtain a plurality of differences $w_i - \overline{w}$ of said scattering angles $w_i$ and said average angle $\overline{w}$, multiplying the absolute values $|w_i - \overline{w}|$ of each of said differences by the respective of said corrected standardized detector signals $p_i$ to obtain products $|w_i - \overline{w}| . pi$, and summing up the plurality of said products $|w_i - \overline{w}| . pi$ to obtain said characteristic value $S_1$ of roughness and structure, respectively.

21. Method for determining the roughness and structure, respectively, of a surface area of workpieces, particularly of metallic workpieces, wherein said method comprises:

(a) directing a beam of light, the rays of which are substantially parallel and substantially perpendicular onto the surface area to be examined (b) detecting the light scattered from said surface area at each one scattering angle of a plurality of scattering angles $w_i$ by means of an array of n detectors;

(c) measuring the individual detector signals $D_i$ of each of the detectors to obtain a plurality of detector signals;

(d) determining corrected standardized detector signals $p_i$ by multiplying each one of said detector signals $D_i$ by each one of individual correction factors $g_i$ associated to each one of said detectors, summing up the obtained products $D_i.g_i$, and dividing each of said products $D_i.g_i$ by the sum of said products $D_i.g_i$, to obtain said corrected standardized detector signals $p_i$;

(e) determining an average angle $\overline{w}$ of the scattered light from the corrected standardized detector signals $p_i$ and the scattering angles $w_i$, according to the formula:

$$\overline{w} = \sum_{i=1}^{n} w_i \cdot p_i$$

(f) determining a characteristic value $S_2$ of roughness and structure, respectively from the average angle $\overline{w}$ and the values $p_i$ and $w_i$ by subtracting said average single w from each of said individual scattering angles $w_i$ to obtain a plurality of differences $w_i - \overline{w}$ of said scattering angles $w_i$ and said average angle $\overline{w}$, determining the second powers of the absolute values $|w_i - \overline{w}|$ of each of said differences, multiplying second powers of the absolute values $|w_1 - \overline{w}|$ of each of said differences by the respective of said corrected standardized detector signals $p_i$ to obtain products $|w_i - \overline{w}|^2.p_i$, and summing up the plurality of said products $|w_i - \overline{w}S|^2.p_i$ to obtain said characteristic value $S_2$ of roughness and structure, respectively.

* * * * *

UNITED STATES PATENT AND TRADEMARK OFFICE
CERTIFICATE OF CORRECTION

PATENT NO. : 4,859,062
DATED : August 22, 1989
INVENTOR(S) : Gerhard Thurn et al.

It is certified that error appears in the above-identified patent and that said Letters Patent is hereby corrected as shown below:

COLUMN 12, FORMULA SHOULD READ AS FOLLOWS:
LINE 1

$$\bar{w} = \sum_{i=1}^{n} w_i \cdot p_i$$

COLUMN 12, LINE 61, REPLACE $|w_i - \overline{w}S|^2 \cdot p_i$ WITH $|w_i - \bar{w}|^2 \cdot p_i$ Signed and Sealed this Twenty-first Day of August, 1990

Attest:

HARRY F. MANBECK, JR.

*Attesting Officer*     *Commissioner of Patents and Trademarks*